(12) United States Patent
O'Neil

(10) Patent No.: US 6,308,598 B1
(45) Date of Patent: Oct. 30, 2001

(54) MODULAR TORQUE-LIMITING DRIVER SYSTEM FOR MEDICAL APPLICATIONS

(76) Inventor: Michael J. O'Neil, 1588 Olde Kings Hwy., West Barnstable, MA (US) 02668

( * ) Notice: Subject to any disclaimer, the term of this patent is extended or adjusted under 35 U.S.C. 154(b) by 0 days.

(21) Appl. No.: 09/197,594

(22) Filed: Nov. 23, 1998

(51) Int. Cl.[7] ................................................. B25B 23/14
(52) U.S. Cl. .................................................. 81/467; 81/439
(58) Field of Search ............................ 81/467, 471, 438, 81/439, 441

(56) References Cited

U.S. PATENT DOCUMENTS

| 4,215,600 | * | 8/1980 | Kesselman | 81/471 |
|---|---|---|---|---|
| 4,420,281 | * | 12/1983 | Dehoff | 411/392 |
| 4,838,264 | * | 6/1989 | Bremer et al. | 128/303 B |
| 5,158,458 | | 10/1992 | Perry | 433/141 |
| 5,176,050 | * | 1/1993 | Sauer et al. | 81/471 |
| 5,295,831 | * | 3/1994 | Patterson et al. | 433/141 |
| 5,299,474 | * | 4/1994 | Hohmann et al. | 81/471 |
| 5,347,894 | * | 9/1994 | Fischer | 81/471 |
| 5,368,480 | | 11/1994 | Balfour et al. | 433/141 |
| 5,735,668 | * | 4/1998 | Klein | 415/172.1 |
| 5,868,047 | * | 2/1999 | Faust et al. | 81/438 |
| 5,964,011 | * | 10/1999 | Ruston et al. | 16/239 |

\* cited by examiner

*Primary Examiner*—Joseph J. Hail, III
*Assistant Examiner*—David B. Thomas
(74) *Attorney, Agent, or Firm*—Nutter, McClennen & Fish, LLP

(57) ABSTRACT

A modular torque-applying surgical tool includes a driver member having a proximal handle and a distal end, and a torque-applying insert removably and replaceably attachable to the distal end of the driver member. The torque-applying insert is designed to be deformable when a predetermined level of torque is achieved, or when the insert is subjected to a torque in excess of a predetermined magnitude such that the insert is effective to apply to a driven member a predetermined minimum torque.

20 Claims, 7 Drawing Sheets

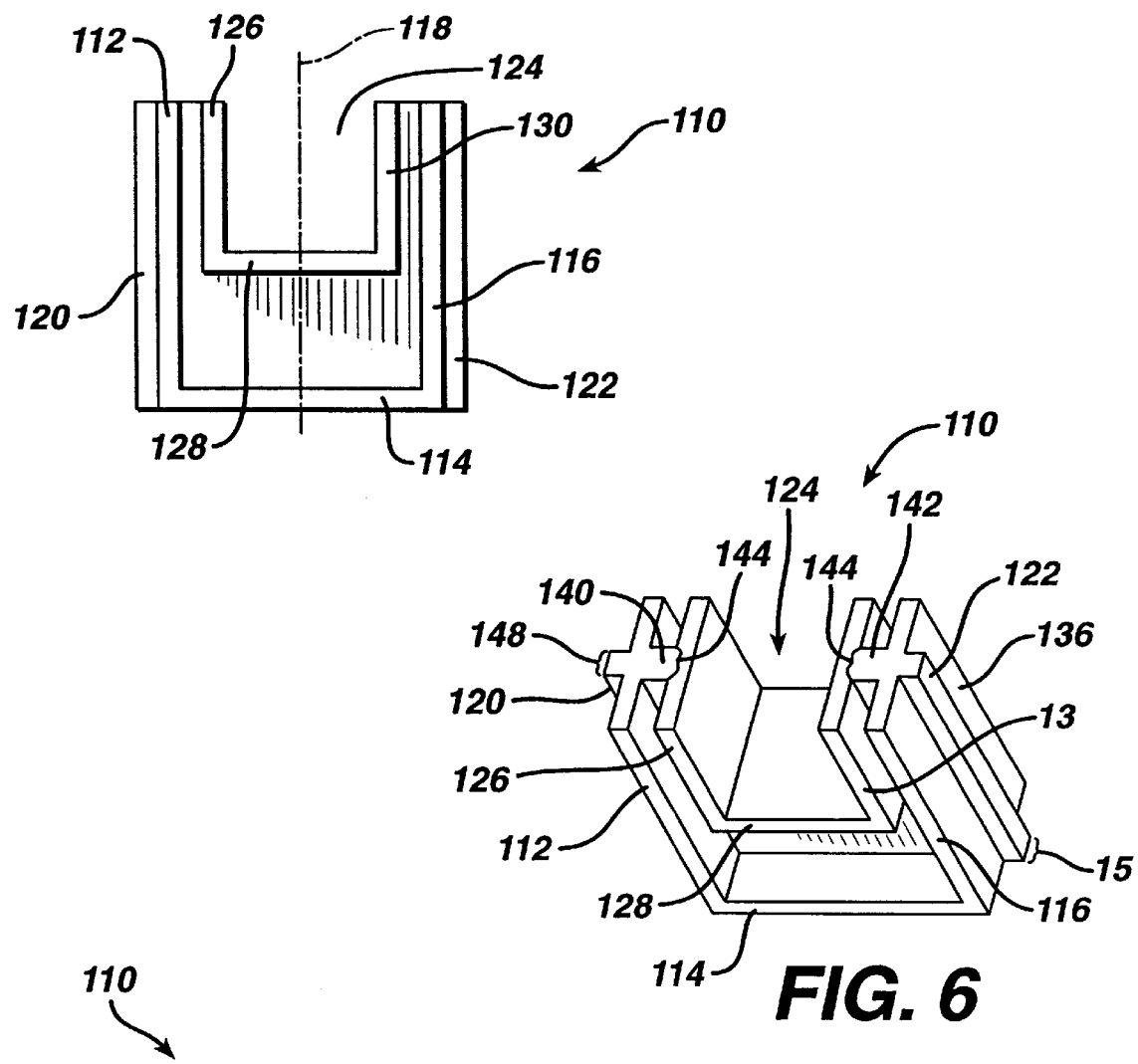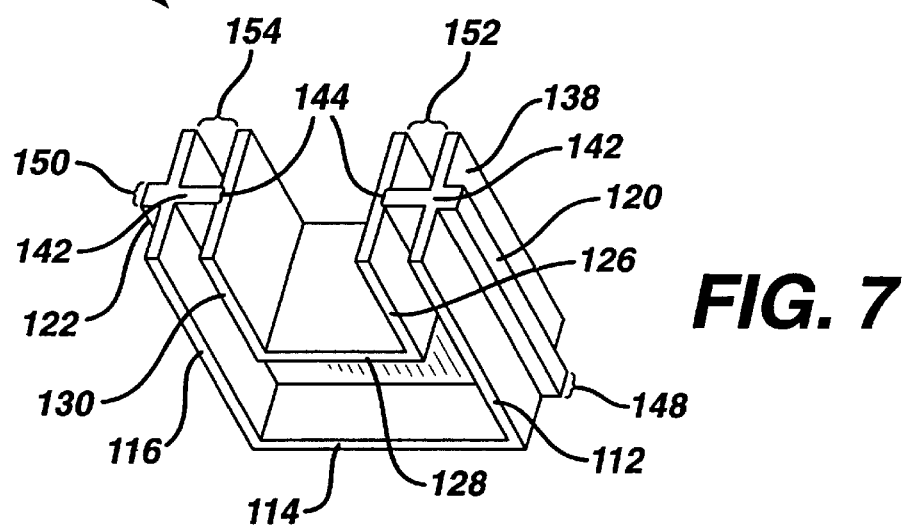

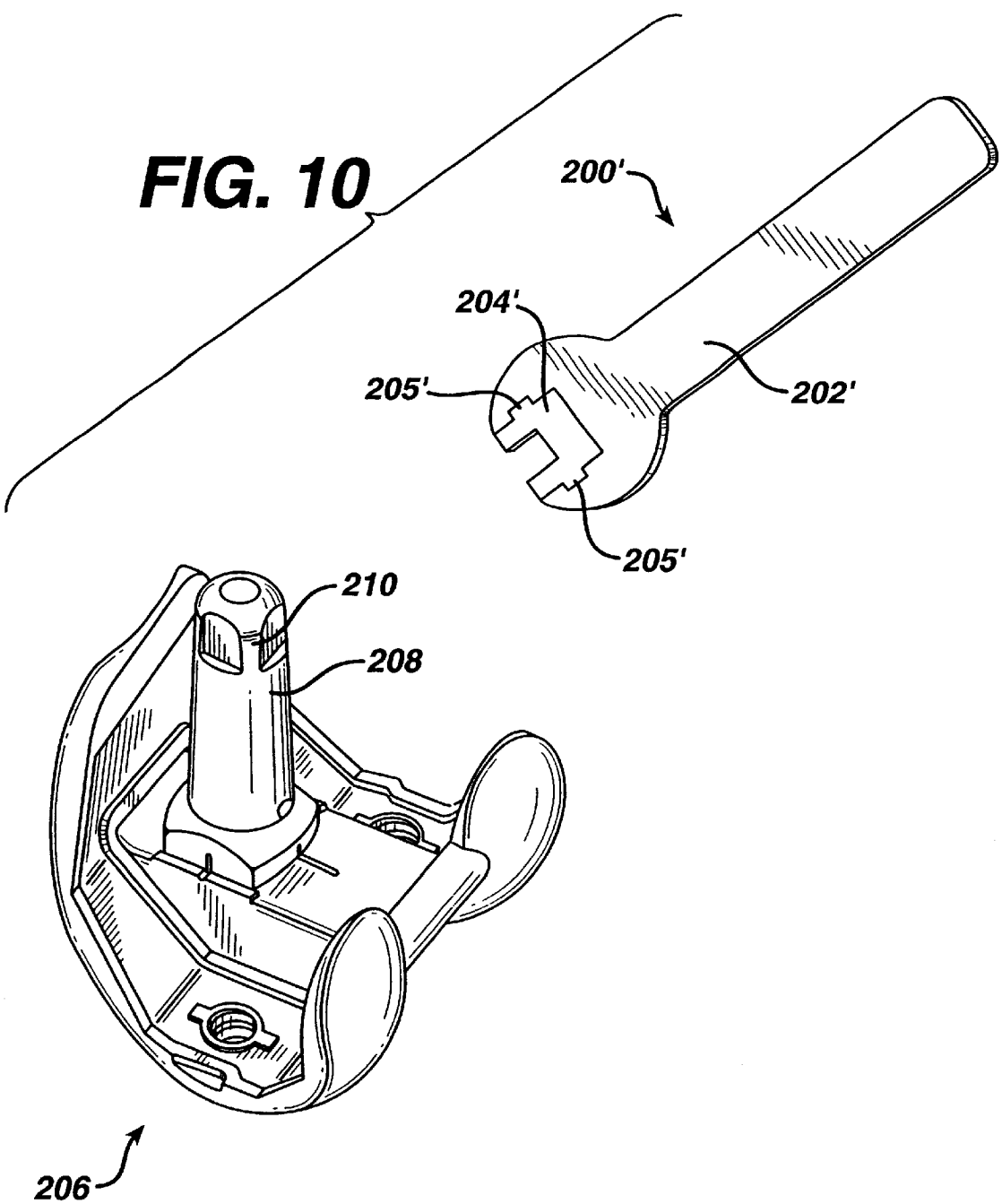

MODULAR TORQUE-LIMITING DRIVER SYSTEM FOR MEDICAL APPLICATIONS

CROSS-REFERENCE TO RELATED APPLICATIONS

Not applicable.

STATEMENT REGARDING FEDERALLY-SPONSORED RESEARCH

Not applicable.

FIELD OF THE INVENTION

The invention relates to a device and system to facilitate the application of the proper level of torque to an implantable component during a medical procedure.

BACKGROUND OF THE INVENTION

Some surgical procedures, such as those involving installation of a joint prosthesis, rely on the use of components that must be securely attached to other components, such as a prosthetic device. If, in attaching a component, the component is either oversecured or undersecured, there can be associated negative effects. For example, an undersecured component may loosen, while an oversecured component may impart an undesirable amount of stress to one or both of the components.

Normally, the attachment of an implant component to another implant component and/or to a prosthetic device is done using devices and methods that impart assembly torque throughout the attachment process. A certain level of torque is required to properly secure a component. However, it is often difficult to perceive, either visually, tactually, or otherwise, when the proper level of torque has been imparted on a component and, in turn, when the component has been securely attached.

To address this perception problem, devices have been developed to help ensure that a consistent or limited assembly torque is imparted on components in order to properly secure torque-applied components to other components. Among these devices are torque-limiting drivers that are calibrated to impart a desired level of torque to a component during the attachment of the component to another component such as a prosthetic device.

Such known torque limiting drivers often suffer from two notable disadvantages. First, it is costly to fabricate drivers to use on components with wide-ranging sizes and geometries. Secondly, such drivers may encounter unwanted drift or change in the calibrated torque. Such drift is believed to be due to constant reuse and steam sterilization following use of the drivers. The torque drift of the calibrated torque of a torque-limiting driver necessitates the costly replacement of the driver or the recalibration of the driver. If drift of the calibrated torque is undetected or ignored, the success of the surgical procedure or the integrity of the prosthetic device can be compromised.

Therefore, a need exists for a device or system that will allow for the achievement and detection of a secure attachment of an implant component to another component, such as a prosthetic device, without allowing for an accompanying risk of oversecuring or undersecuring the component.

SUMMARY OF THE INVENTION

The present invention provides a modular torque-applying surgical tool which includes a driver member that has a proximal handle and a distal end, and a torque-applying insert that is removably and replaceably mountable to the distal end of the driver member. The torque-applying insert is designed to be deformable when a predetermined level of torque is achieved, or when the insert is subjected to a torque in excess of a predetermined magnitude, such that the insert is effective to apply to a driven member a predetermined minimum torque.

In one embodiment of the present invention, the torque-applying insert is adapted for use with a universal or allen wrench-type driver. The insert may have a male hex head that is dimensioned to be matable with a female hex receptacle on a driven member. In another embodiment of the present invention, the torque-applying insert is a substantially U-shaped wrench-like member that is adapted to be placed within a universal wrench-type driver member so as to engage with a driven member.

For both the universal driver and a universal wrench-type driver embodiments, a selection of inserts, having different sizes and strengths, will be provided. Each insert is intended to be a disposable, single-use insert. This enables a single driver member to be mated with an insert of a suitable size and with suitable properties to be used in a desired application. Also, in either embodiment of the present invention, the predetermined level of torque that is indicated by the deformation of the torque-applying insert may correspond to a minimum or maximum level of torque or to another predetermined level of torque that, when achieved or exceeded, causes the insert to roll over, crack, fracture or otherwise provide a visual, tactile or aural indication of the achievement or exceeding of that predetermined level of torque.

BRIEF DESCRIPTION OF THE DRAWINGS

A more complete understanding of the present invention and the attendant advantages and features thereof will be more readily understood by reference to the following detailed description when it is considered in conjunction with the accompanying drawings, wherein:

FIG. 5 is a plan view of an alternate embodiment of a torque-applying insert in accordance with the present invention;

FIG. 6 is a perspective view of the torque-applying insert of FIG. 5;

FIG. 7 is a perspective view of an alternate embodiment of the torque-applying insert of the type shown in FIG. 5;

FIG. 10 is a perspective view of a component and an alternate embodiment of the torque-applying tool of FIG. 9.

DETAILED DESCRIPTION OF THE INVENTION

Figure 1:
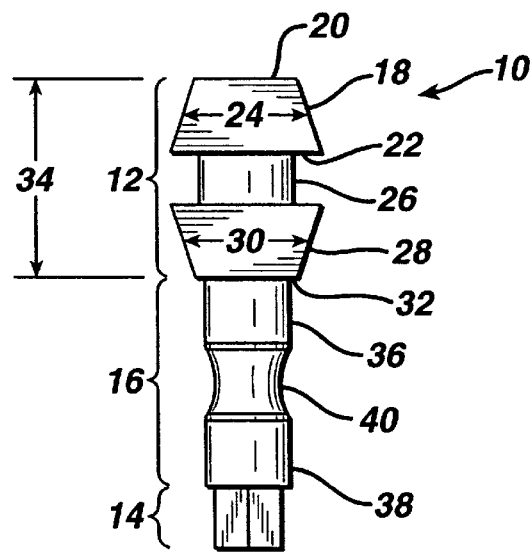
FIG. 1 is a plan view of a torque-applying insert in accordance with the present invention.

A torque-limiting insert in accordance with the present invention is shown in FIGS. 1–4. The insert 10 has a proximal region 12 that is adapted for mating within a driver member and a distal region 14 that engages and applies torque to a driven member. An intermediate region 16 is disposed between the proximal and distal regions 12, 14.

The proximal region 12 may be of virtually any size and shape that renders it suitable to be mated with a driver member, preferably in an interference fit. In the illustrated embodiment, the proximal region 12 includes a tapered first region 18 that extends from end wall 20 to shoulder 22. First region 18 is tapered such that its diameter 24 decreases from a maximum adjacent the shoulder 22 to a minimum adjacent the end wall 20.

In one embodiment, the proximal region 12 may also include an intermediate zone 26 distally adjacent to the shoulder 22 of the first tapered region 18, and a second tapered region 28 that is distally adjacent to the intermediate zone. The second tapered region 28 has a taper that is the reverse of that of the first region 18. That is, region 28 has a diameter 30 that tapers from a maximum adjacent the intermediate zone 26 to a minimum at a distal end 32 thereof.

One of ordinary skill in the art will readily understand that the dimensions of the proximal region 12 may be varied depending upon the requirements of a given application of the present invention. By way of example, however, the proximal region 12 may have a length 34 of about 5.0 millimeters to 15.0 millimeters. The diameter of regions 18 and 28 may taper from a maximum of about 10.0 millimeters to 25.0 millimeters, to a minimum of about 2.0 millimeters to 5.0 millimeters. Generally, the angle of taper is about 20° to 30°. Each of regions 18 and 28 may have a length of about 1.0 millimeters to 6.0 millimeters.

The intermediate region 16 is generally cylindrical and extends over a length of about 5.0 millimeters to 25.0 millimeters. Region 16 includes a first cylindrical zone 36 and a second cylindrical zone 38. Optionally, a reduced diameter zone 40 may be disposed between zones 36 and 38. Where zone 40 is present, each of zones 36, 38, 40 may have a length in the range of about 2.0 millimeters to 10.0 millimeters. Reduced diameter zone 40 can be useful to promote fracture or failure of the insert 10 within the reduced diameter zone when a predetermined minimum level of torque is achieved or exceeded.

Figure 1A:
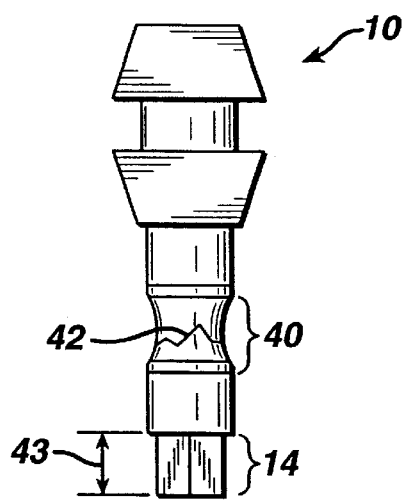
FIG. 1A is a plan view of the torque-applying insert of FIG. 1 with a fracture therein.

FIG. 1A illustrates a possible mode of failure of the insert 10 in which a crack 42 has propagated across the reduced diameter zone 40. The formation of the crack 42 within the zone 40 would be noticeable either visually, and/or tactually, and/or aurally, or otherwise, and would prevent further application of torque to a driven member.

The distal region 14 of the insert 10 generally is substantially hexagonal in shape and in the form of a male "hex head" and is dimensioned to be inserted within a female hexagonal receptacle of a driven member, as described below. The distal region 14 will generally have a longitudinal length 43 of between about 1.0 millimeters and 5.0 millimeters. One of ordinary skill in the art will appreciate, however, that the distal region 14 may have another shape while still allowing insert 10 to be effective to impart torque to a driven member.

The insert 10 may be designed so as to provide indications of the achievement or exceeding of a predetermined level of torque other than by fracture or failure in reduced diameter zone 40. For example, the distal region 14 of the insert 10 could be engineered to deform and roll over the driven member without applying additional torque, upon the achievement of a predetermined level of torque. Regardless of how the insert 10 fails to deliver further torque to a driven member, one of ordinary skill in the art will understand that the insert is intended to be a disposable, single-use element.

One of ordinary skill in the art will understand that the shape and dimensions of the insert 10 can be designed to promote failure at a certain torque level. Further, the choice of materials from which the insert 10 can be made also affects the predetermined minimum level of torque that can be applied by the insert. Also, the material selection is dependent upon several characteristics including, but not limited to, torque desired and the technique used to sterilize the insert 10.

The insert 10 can be made of a variety of materials, including polymers, ceramics, composites and metals or metal alloys. Exemplary polymers include polypropylene, polyurethane, ultra-high molecular weight polyethylene, polyethylene, polysulfones, polyethersulfones and polyphenylsulfones. Exemplary metals include cobalt, titanium and aluminum, and exemplary metal alloys include 400 series stainless steel, cobalt alloys, aluminum alloys and titanium alloys.

Figure 2:
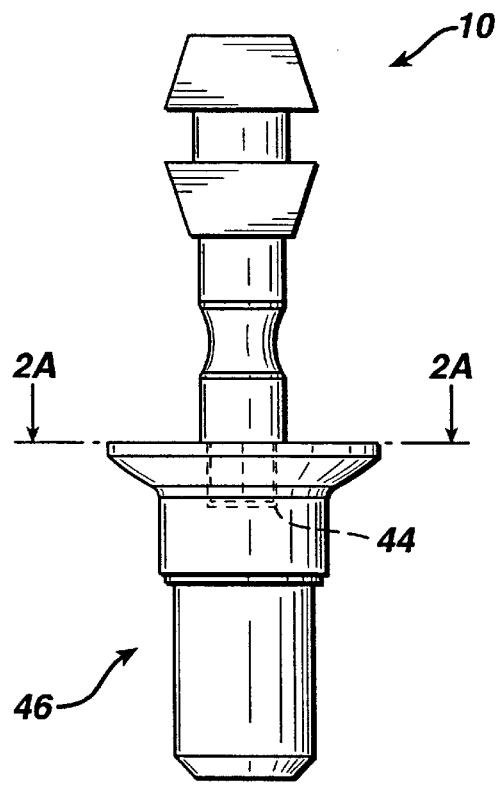
FIG. 2 is a side view of the torque-applying insert of FIG. 1 operably associated with a driven member.
Figure 2A:
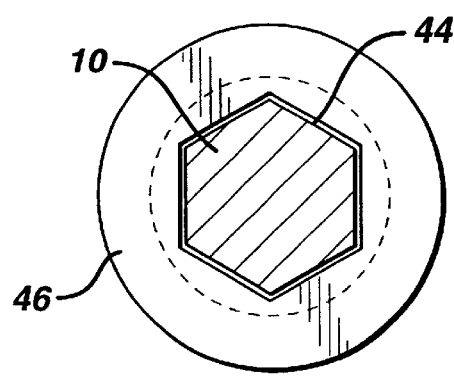
FIG. 2A is a sectional view at line 2A—2A of the insert-driven member assembly of FIG. 2.

Referring now to FIGS. 2 and 2A, the torque-applying insert 10 is shown having been inserted into a female receptacle 44 of a driven member 46. The driven member 46 may generally be any component which needs to be attached to another component, such as a prosthetic device, without being oversecured or undersecured. In the illustrated embodiment of FIGS. 1–4, the driven member 46 is a set screw to be used with a joint prosthesis component.

Figure 3:
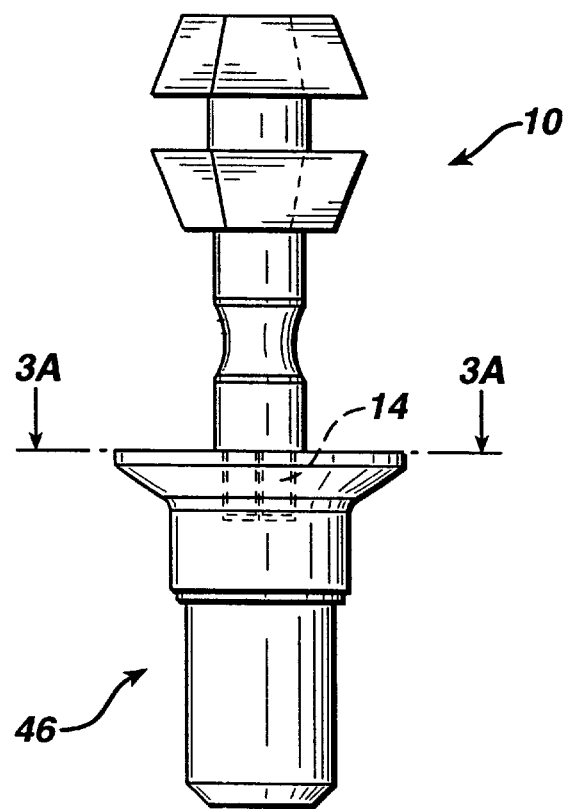
FIG. 3 is a side view of the insert-driven member assembly of FIG. 2 after applying a level of torque to the driven member in excess of a predetermined amount.
Figure 3A:
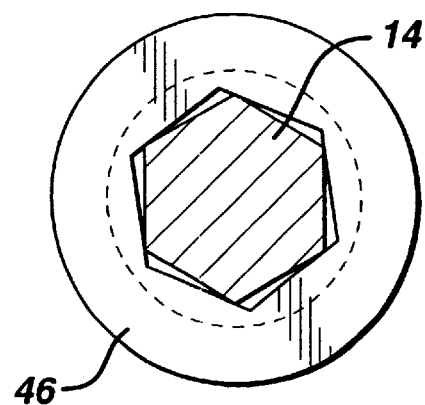
FIG. 3A is a sectional view at line 3A—3A of the insert-driven member assembly of FIG. 3.

Referring now to FIGS. 3 and 3A, the torque-applying insert 10 is shown following the application of torque at or above a predetermined minimum level of torque to the driven member 46. As a result of applying this amount of torque to the driven member 46, the distal region 14 of the insert has deformed and is no longer capable of applying torque to the driven member.

Figure 4:
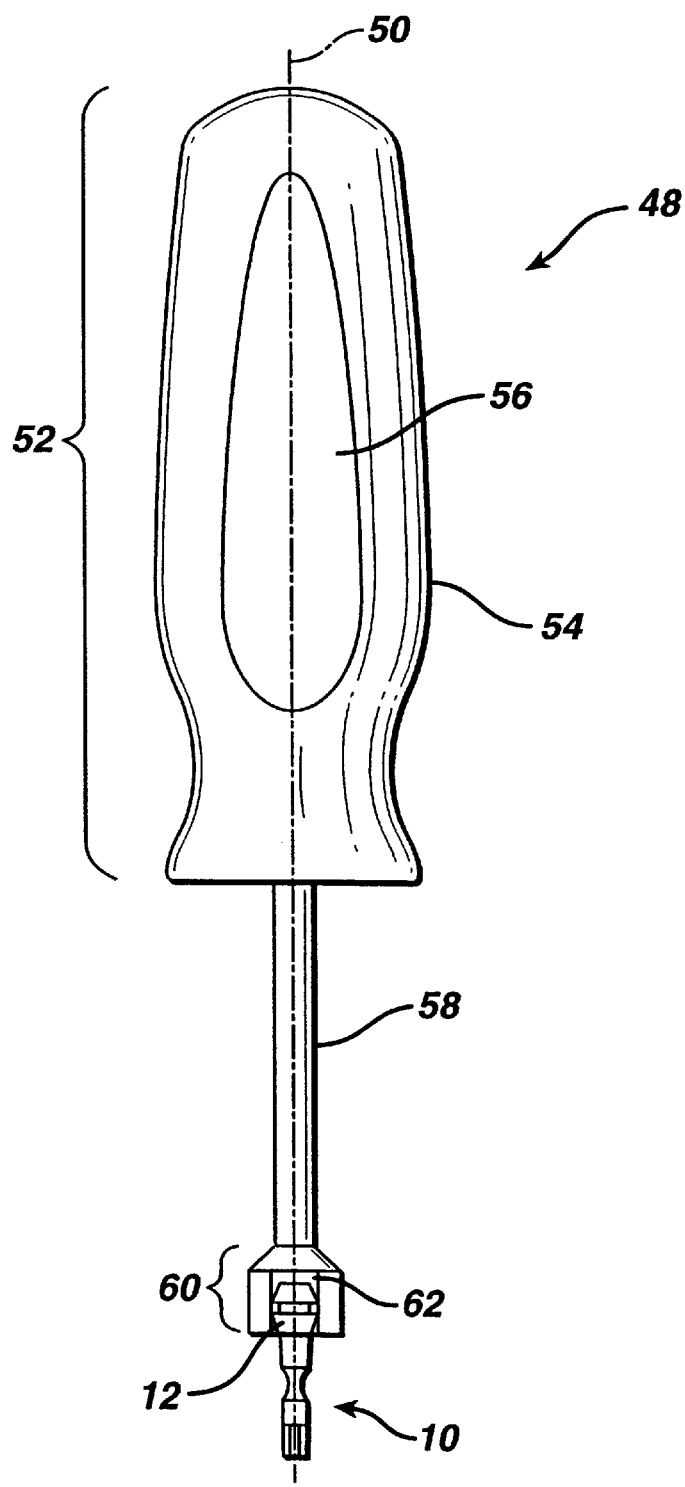
FIG. 4 is a side view, with partial cut-away, of the torque-applying insert of FIG. 1 disposed within a driven member.

FIG. 4 illustrates the torque-applying insert 10 of FIGS. 1–3 mounted within driver member 48. The driver member 48 is an elongate member having a longitudinal axis 50. A proximal portion 52 of the driver member 48 includes a handle 54 with gripping area 56. An elongate rod 58 extends from handle 54 and terminates in a distal, head end 60 of the driver member 48. The distal end 60 includes an insert-receiving socket 62 within which the proximal region 12 of an allen-wrench insert 10 is removably and replaceably mounted. Preferably, proximal region 12 is securely held within socket 62 in an interference fit that, at least up to the predetermined minimum level of torque for a given insert, prevents rotation of the insert 10 independent of the driver member 48. Further, one of ordinary skill in the art will appreciate that the proximal portion 52 of the driver member 48 may have other features, in addition to or instead of gripping area 56, or may have a different geometry in order to facilitate the gripping of the handle 54.

Referring now to FIGS. 5–9, an alternate embodiment of the torque-applying insert 110 is shown. The insert 110 is a substantially U-shaped wrench-like member that has three sides 112, 114, 116 and a longitudinal axis 118. Sides 112 and 116 are substantially parallel and approximately equal, while side 114 is substantially transverse to sides 112 and 116 and may or may not be equal in length to sides 112 and 116. Each of sides 112 and 116 of the insert 110 has a rib member 120, 122 protruding therefrom to facilitate the removable and replaceable mounting of the insert 110 within a driver member.

The insert 110 also has a substantially U-shaped, inner driven member-receiving area 124. The inner area 124 of the insert 110 is defined by three sides 126, 128, 130 and it may be aligned with the longitudinal axis 118 of the insert. Sides 126 and 130 are substantially parallel and approximately equal, while side 128 is substantially transverse to sides 126 and 130 and may or may not be equal in length to sides 112 and 116.

As shown in FIGS. 6 and 7, the insert 110 has a pair of sidewalls, 136, 138 on which, respectively, the rib members 120, 122 lie. Preferably, each of the rib members 120, 122 is centrally aligned along each of the sidewalls 136, 138 of the insert 110 and will have a longitudinal length approximately equal to the sides 112, 116 of the insert 110 from which it protrudes.

Also as shown in FIGS. 6 and 7, sides 112 and 116 of the insert 110 may be spaced apart from sides 126 and 130, respectively, of the inner area 124 of the insert. Preferably, side 112 of the insert 110 is spaced apart from side 126 of the inner area 124 of the insert by a first beam member 140, while side 116 of the insert is spaced apart from side 130 of the inner area of the insert by a second beam member 142. Generally, the first and second beam members 140, 142 are substantially transverse to each of the sides of the insert 110 and the sides of the inner area 124 of the insert which they connect, and thus form I-beam geometries when viewed with sides 112, 126 and 116, 130. Preferably, the first and second beam members 140, 142, respectively, will be centrally aligned between each of the sides 112, 126 and 116, 130 which they connect, and are thus also aligned with, respectively, rib member 120 and rib member 122.

Each of the first and second beam members 140, 142 has a thickness 144. The thickness 144 may be varied in order to influence the predetermined level of torque that needs to be achieved or exceeded for the insert 110 to deform. Generally, the greater the thickness 144 of the first and second beam members 140, 142, the greater the increasing effect on the amount of torque required for the insert to deform.

FIGS. 6 and 7 are examples of inserts with beam members 140, 142 having a different thickness. For example, in FIG. 6, first and second beam members 140, 142 each have a thickness 144 that is greater than a corresponding thickness 148 of rib member 120 or 122. In FIG. 7, the first and second beam members 140, 142 each have a thickness 144 that is less than the thickness of the first and second beam members 140, 142 shown in FIG. 6, and less than the corresponding thickness 148, 150 of rib member 120 or 122.

One of ordinary skill in the art will appreciate that the material(s) from which the insert 110 is made, and the values for its dimensions, will vary depending on the driver member into which the insert is removably and replaceably mounted, and the driven member onto which the insert imparts torque; however, certain materials and dimensions are preferred.

The insert 110 can be made of a variety of materials, including polymers, ceramics, composites and metals or metal alloys. Exemplary polymers include polypropylene, polyurethane, ultra-high molecular weight polyethylene, polyethylene, polysulfones, polyethersulfones and polyphenylsulfones. Exemplary metals include cobalt, titanium and aluminum, and exemplary metal alloys include 400 series stainless steel, cobalt alloys, aluminum alloys and titanium alloys.

The insert 110 also has a general range of dimensions. In an exemplary embodiment, sides 112, 114, 116 of the substantially U-shaped insert may all be equal and may range between about 5.0 millimeters and 20.0 millimeters. The sides 126, 128, 130 may be equal and may range between about 5.0 millimeters and about 20.0 millimeters. Each side 112, 114, 116, 126, 128, 130 has a thickness that is equal and between about 0.5 millimeters and 4.0 millimeters. Rib members 120, 122 have thicknesses 148 that are equal and between about 0.5 millimeters and 4.0 millimeters. First and second beam members 140, 142 have a thickness 144 that are equal and between about 0.25 millimeters and 4.0 millimeters, and have lengths 152, 154 that are equal and between about 1.0 millimeters and 5.0 millimeters.

Regardless of the material from which the insert 110 is made, and the dimensions it has, the insert should be deformable once a predetermined level of torque on the insert 10 is achieved or exceeded while the insert is within a driven member. Generally, an insert such as that shown in FIG. 5 will deform and roll over the driven member once the predetermined level of torque on the insert is achieved or exceeded. The insert 50, however, may indicate the achievement or exceeding of a predetermined level of torque other than by rolling over, such as, by the formation of a crack, or the fracture of the insert after the formation and propagation of a crack in the insert.

Figure 8:
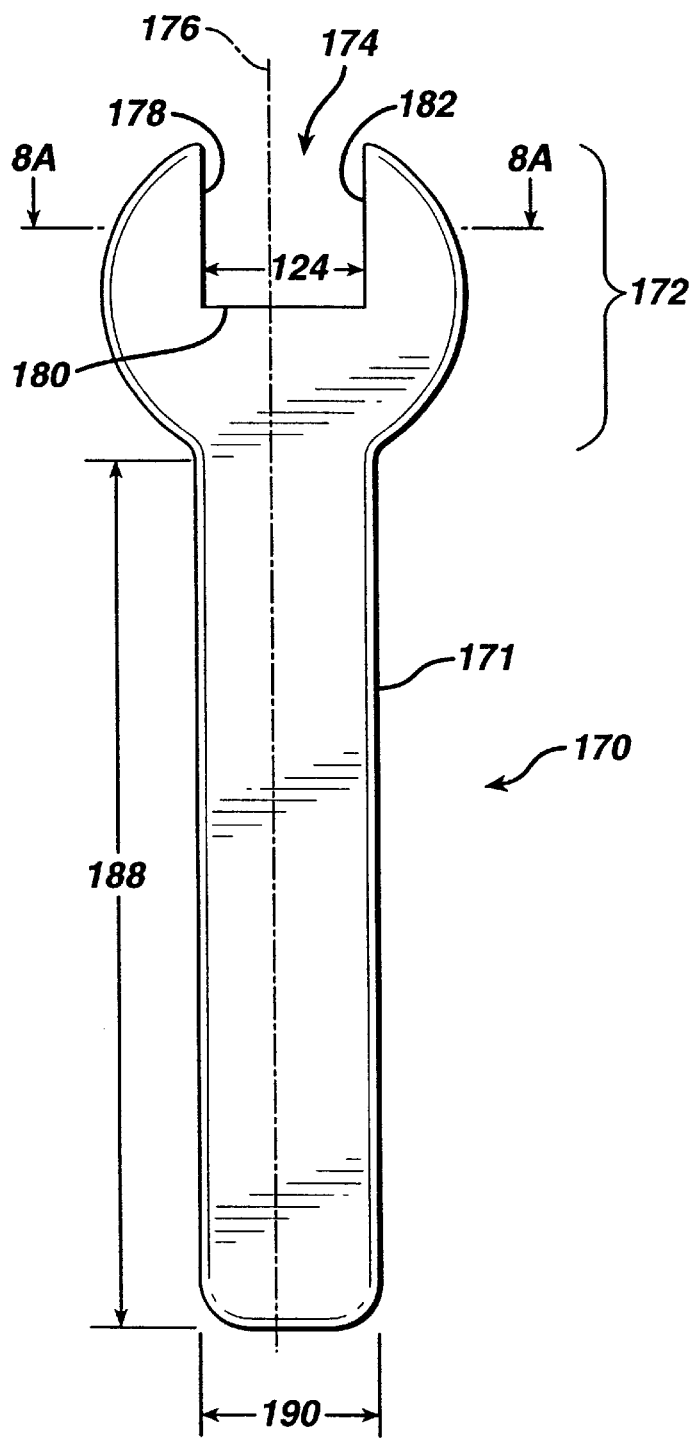
FIG. 8 is a plan view of a driver member usable in conjunction with the torque-applying insert of FIGS. 5–7.
Figure 8A:
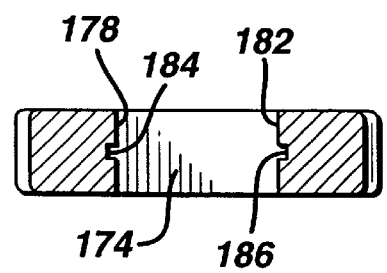
FIG. 8A is sectional view of the driver member of FIG. 8 taken along the line 8A—8A.

Referring now to FIGS. 8 and 8A, a driver member within which the insert of FIGS. 5–7 is removably and replaceably mountable is shown. The driver member 170 is generally a universal wrench in the form of an elongate member extending along a longitudinal axis 176. Driver member 170 has a proximal handle 171 and a distal, head end 172 having an inner, insert receiving area 174 defined by three sides.

In the embodiment shown in FIG. 8A, each of side walls 178, 182 of the insert-receiving socket 174 has a mating channel 184, 186 for receiving rib members (as shown in FIGS. 5–7) of the insert. Each mating channel 184, 186 is preferably identical and is oriented so as to be substantially parallel to the longitudinal axis 176 of the driver member 170. Further, each mating channel 184, 186 preferably extends along the entire longitudinal length of the side walls 178, 182 to facilitate the removable and replaceable mounting of the torque-applying insert 110 within the driver member 170.

One of ordinary skill in the art will appreciate that the dimensions of the driver member 170 will vary depending on the insert that is removably and replaceably mounted therein, and the driven member onto which the insert is to impart torque.

The handle 171 should have dimensions suitable for grasping, and for imparting torque on the insert. Generally, the handle 171 has a longitudinal length 188 between about 5.0 centimeters and 20.0 centimeters and a width 190 between about 1.0 centimeters and 5.0 centimeters. The distal, head end 172 of the driver in which the insert-receiving socket 174 is defined is generally circular, minus the insert receiving socket area.

Figure 9:
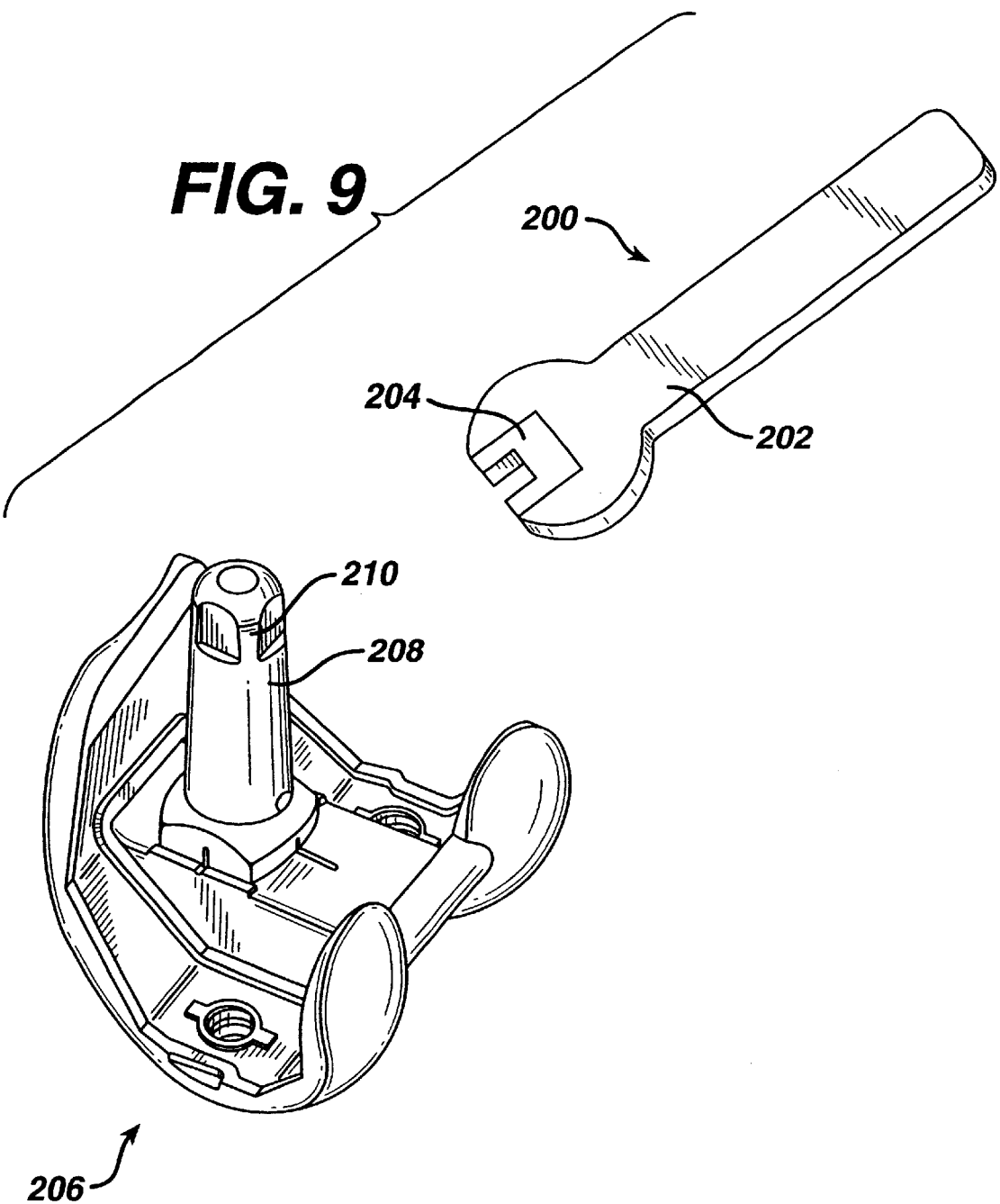
FIG. 9 is a perspective view of a torque-applying tool and a component in accordance with the present invention.

Referring now to FIG. 9, a torque-applying tool 200 and an implant component 206 driven member are shown. The torque applying tool 200 includes a driver member 202 as shown in, and described above with respect to, FIGS. 8 and 8A, and a removable and replaceable torque-applying insert 204, as shown in, and described above with respect to, FIGS. 5–7. Also shown in FIG. 9 is a femoral attachment component 206 that has a driven member 208 with an end 210 that is adapted to engage the torque-applying tool 200 and to have torque applied thereto.

Once sufficient torque is applied to the end 210 of the driven member 208 by the driver member 202, the torque-applying tool 200 will generally signal that a predetermined level of torque has been exceeded or achieved by deforming so as to roll over the driven member without permitting the application of further torque to the driven member. However, the tool 200 may also indicate that a predetermined level of torque has been achieved in another way, such as by the formation and/or propagation of a crack within, or fracture of, the insert 204.

Referring now to FIG. 10, an alternate embodiment of a torque-applying tool 200' is shown with an implant component 206. The tool 200' includes a driver member 202' and a removable and replaceable torque-applying insert 204'. Insert 204' is similar to the removable and replaceable torque-applying insert of FIGS. 5–7, except that the insert 204' does not have rib members that mate from the front end of the driver member 202' into the mating channels of the driver member. Insert 204' instead has side-mounted flanges 205' that snap into corresponding slots in driver member 202'. In this embodiment, the insert 204' may be snapped into a top surface of the driver member 202', rather than slid into the driver member from the front end thereof as in the embodiment of FIG. 9.

It is understood that the invention contemplates a system that includes a plurality of disposable, single-use, torque-applying inserts that are removably and replaceably matable or mountable within the insert receiving socket of the driver member. The inserts may be provided in different sizes and with different shapes. The various inserts can be designed to apply a different, predetermined magnitude of torque such that each insert is effective to apply to a driven member a predetermined minimum torque.

The following non-limiting example serves to further illustrate features of the invention.

EXAMPLE

Torque-applying inserts 110 of the type shown in FIGS. 5–7 were prepared. Three samples of a first insert were produced from ultra-high molecular weight polyethylene. These first samples had beam member (140, 142) thicknesses (144) of approximately 0.0625 inch (1.59 millimeters). Three samples of a second insert were also produced from ultra-high molecular weight polyethylene. These second samples had beam member (140, 142) thicknesses (144) of approximately 0.125 inch (3.18 millimeters).

Each sample was tested to determine the peak (maximum) torque able to be transmitted prior to deformation. Beyond the point of deformation, the inserts could not longer transmit torque. The results are summarized in Table I below:

TABLE I

| Type of Torque-Applying Insert | Peak Torque (inch-lbs) | Average Peak Torque (inch-lbs) |
| --- | --- | --- |
| First (Sample #1) | 8.4 | |
| First (Sample #2) | 9.0 | |
| First (Sample #3) | 9.0 | |
| First (Samples #1–3) | | 8.8 |
| Second (Sample #1) | 13.8 | |
| Second (Sample #2) | 13.8 | |
| Second (Sample #3) | 10.2 | |
| Second (Samples #1–3) | | 12.6 |

One of ordinary skill in the art will readily appreciate that the driver member and insert systems of the invention may have dimensions and properties that fall outside of the ranges given above in order to be adapted to be used in a wide range of situations with a wide range of materials and equipment. Further, while the invention has been shown and described with respect to exemplary embodiments thereof, various other changes, omissions and additions in form and detail thereof may be made therein without departing from the spirit and scope of the invention.

What is claimed is:

1. A modular torque-applying surgical tool, comprising:
   a driver member having a proximal handle and a distal end; and
   a separate torque-applying insert removably and replaceably matable to the distal end of the driver member in an interference fit, and the insert being deformable when subjected to a torque at or above a predetermined magnitude such that a distal end of the insert is adapted to directly contact and is effective to apply to a driven member a predetermined minimum torque.

2. The torque-applying tool of claim 1, wherein the distal end of the driver member has an insert-receiving socket within which the torque-applying insert is removably and replaceably mounted.

3. The torque-applying tool of claim 2, wherein the deformation of the torque-applying insert that results upon achieving a torque at or above a predetermined magnitude prevents the driver member from applying further torque to the driven member.

4. The torque-applying tool of claim 3, wherein the driver member is prevented from applying further torque to the driven member by the torque-applying insert rolling over the driven member.

5. The torque-applying tool of claim 3, wherein the driver member is prevented from applying further torque to the driven member by the fracture of the torque applying insert.

6. The torque-applying tool of claim 3, wherein the torque-applying insert is a substantially U-shaped wrench-like member having an inner, driven member-receiving area defined by three sides.

7. The torque-applying tool of claim 3, wherein the torque-applying insert is an allen wrench insert having a mounting end removably and replaceably mountable within the distal end of the driver member and a distal, head end having an allen-type head.

8. The torque-applying tool of claim 1, wherein the driver member is a universal wrench.

9. The torque-applying tool of claim 1, wherein the driver member is a universal driver.

10. The torque-applying tool of claim 3, wherein the torque-applying insert is made from a material selected from a group consisting of polymers, ceramics, composites, metals and metal alloys.

11. The torque-applying tool of claim 10, wherein the torque-applying insert is made from a polymer selected from the group consisting of ultra-high molecular weight polyethylene, polypropylene, polyurethane, polyethylene, polysulfones, polyethersulfones and polyphenylsulfones.

12. The torque-applying tool of claim 10, wherein the torque-applying insert is made from a metal selected from the group consisting of cobalt, titanium and aluminum.

13. The torque-applying tool of claim 10, wherein the torque-applying insert is made from a metal alloy selected from the group consisting of 400 series stainless steel, cobalt alloys, titanium alloys and aluminum alloys.

14. The torque-applying tool of claim 4, wherein the insert receiving socket of the driver member is a substantially U-shaped socket defined by a pair of substantially parallel side walls and end wall, the side walls each having a mating channel formed therein that is oriented so as to be substantially parallel to a longitudinal axis of the driver member.

15. The torque-applying tool of claim 14, wherein the insert has opposed, substantially parallel side walls and an end wall, each side wall having a rib member protruding therefrom that is matable within the mating channel of the insert receiving socket.

16. A modular torque-applying surgical tool system, comprising:

a driver member having a proximal handle and a distal end, the distal end including an insert receiving socket; and a plurality of separate torque-applying inserts, each of the inserts being removably and replaceably matable within the insert receiving socket of the driver member in an interference fit, and each insert being deformable when subjected to a torque level at or above a different, predetermined magnitude such that a distal end of each insert is adapted to directly contact and is effective to apply to a driven member a predetermined minimum torque.

17. The system of claim 16, wherein deformation of the insert prevents application of additional torque by the driver member.

18. The system of claim 17, wherein the driver member is a universal wrench.

19. The system of claim 17, wherein the driver member is a universal driver.

20. The system of claim 18, wherein at least one of the torque-applying inserts is substantially U-shaped.

* * * * *